United States Patent [19]

Wilson et al.

[11] Patent Number: 5,019,232

[45] Date of Patent: May 28, 1991

[54] MEDIUM FOR ELECTROPHORESIS

[75] Inventors: Theresa J. Wilson; Louis C. Haddad, both of St. Paul; Donald F. Hagen, Woodbury, all of Minn.

[73] Assignee: Minnesota Mining and Manufacturing Company, St. Paul, Minn.

[21] Appl. No.: 531,836

[22] Filed: Jun. 1, 1990

[51] Int. Cl.$^5$ .................. C25B 1/00; B01D 15/08; C02F 1/28

[52] U.S. Cl. .................. 204/182.8; 204/180.1; 204/299 R; 210/635

[58] Field of Search ........... 204/182.3, 182.9, 182.8; 210/657; 435/182

[56] References Cited

U.S. PATENT DOCUMENTS

| | | | |
|---|---|---|---|
| 3,407,096 | 10/1968 | Landi | 136/86 |
| 3,407,249 | 10/1968 | Landi | 264/49 |
| 3,875,044 | 4/1975 | Renn et al. | 204/299 |
| 3,922,432 | 11/1975 | Renn | 428/327 |
| 4,006,069 | 2/1977 | Hiratsuka et al. | 204/180 |
| 4,153,661 | 5/1979 | Ree et al. | 264/120 |
| 4,373,519 | 2/1983 | Errede et al. | 128/156 |
| 4,460,642 | 7/1984 | Errede et al. | 428/283 |
| 4,565,663 | 1/1986 | Errede et al. | 264/120 |
| 4,589,965 | 5/1986 | Kreisher | 204/182.8 |
| 4,657,656 | 4/1987 | Ogawa | 204/299 |
| 4,718,998 | 1/1988 | Ogawa et al. | 204/299 |
| 4,722,777 | 2/1988 | Ogawa et al. | 204/299 |
| 4,810,381 | 3/1989 | Hagen et al. | 210/502.1 |
| 4,871,671 | 10/1989 | Errede et al. | 435/182 |
| 4,906,378 | 3/1990 | Hagen et al. | 210/635 |

FOREIGN PATENT DOCUMENTS 60-164242 8/1985 Japan.

OTHER PUBLICATIONS

*New Directions in Electrophoretic Methods*, Phillips, Marwhall, Ed., American Chemical Society, Washington, D.C., 1987, pp. 1-20.

*Electrophoresis*, Z. Deyl, Ed., G. Chromatography Library, Elsevier, New York, N.Y., 1979, pp. 1-37.

"Fabric Reinforced Polyacrylamide Gels for Electroblotting", *Electrophoresis*, 6, pp. 349-350, 1985.

Primary Examiner—John F. Niebling
Assistant Examiner—Caroline Koestner
Attorney, Agent, or Firm—Gary L. Griswold; Walter N. Kirn; Lorraine R. Sherman

[57] ABSTRACT

A medium for electrophoresis comprises:
(a) a polytetrafluoroethylene (PTFE) fibril matrix, and
(b) particulate, electrically mobile ions, and sufficient liquid in the interstitial spaces of said matrix to allow for ion transport, the ratio of said particulate to PTFE being in the range of 99:1 to 4:1 by weight, and said ions being present in said liquid in an amount to provide a solution of concentration in the range of 1 to 1000 millimolar.

Preferably the medium is self supporting.

34 Claims, 2 Drawing Sheets

MEDIUM FOR ELECTROPHORESIS

FIELD OF THE INVENTION

This invention relates to electrophoretic media which are self supporting composite structures and a method therefor, the media comprising a polytetrafluoroethylene (PTFE) fibril matrix having liquid, electrically mobile ions, and particulate incorporated therein. In another aspect, a method of using the composite structures in electrophoretic separations is disclosed.

BACKGROUND OF THE INVENTION

Electrophoretic processes are known in the art and provide a means of separating, purifying, and analyzing mixtures.

Electrophoresis is an electromigration separation process based on differences in mobilities of electrically charged particles, solutes, or components of mixture in an electrical field. Species separated are generally charged. Neutral species can be separated if electroendoosmotic flow is present. Generally, there are two types of electrophoresis in use: moving boundary or "free" electrophoresis, in which separation takes place in free solution, and zone electrophoresis in which separation takes place utilizing solid supports. Electrophoresis is discussed in *New Directions in Electrophoretic Methods*, Phillips, Marwhall, Ed., American Chemical Society, Washington, D.C., 1987, pp. 1-20, and in *Electrophoresis*, Z. Deyl, Ed., G. Chromatography Library, Elsevier, New York, N.Y., 1979, pp. 1-37.

Presently, the most common type of electrophoresis is zone electrophoresis wherein certain solid or gel-type supports are used. The support serves as an anticonvection medium that limits free diffusion, and can aid the separation process through physical or chemical interactions with components of the mixture being separated.

Supports generally used in electrophoresis are solids such as paper and cellulose derivatives, and gels which are prepared from acrylamide, starch, agarose, and other materials. Gel electrophoresis is the most widely used form in this separation technique and finds application in analytical and preparative separation of proteins, nucleic acids, and other biological macromolecules. Several forms of gel electrophoresis in use include normal or native gel electrophoresis, denatured/sodium dodecyl sulfate (SDS) electrophoresis, isoelectric focusing (IEF) and immunelectrophoresis, as is known to those skilled in the art.

A conventional gel or gel slab for use in gel electrophoresis must be very thin to optimize speed, resolution, and to minimize localized heating. Thin gels, however, are very fragile and difficult to handle especially when concentrations of the gel material, for example, polyacrylamide, is low. Low concentration gels are necessary for separation of large (high molecular weight) molecules. However, these gels have little structural integrity.

To improve the mechanical stability and handling properties of such fragile gels, heretofor nonconductive support backings have been used. Unfortunately, these backings interfere with uniform transfer of heat generated from the electrical potential and from the resistance of the separation media and they cannot be used in electro-blotting experiments. Moreover, thin gels also have very low sample capacity and are not useful for separations on a preparative scale.

Preparative gel electrophoresis can be performed on a bed of granulated swellable beads such as crosslinked polyacrylamide or other particulates such as crosslinked polydextrans. Preparation of the beds and isolation of products from them is laborious and time consuming. Further, the bed has very little structural integrity.

Composite articles comprising a polytetrafluoroethylene matrix with particulate enmeshed therein have been disclosed. U.S. Pat. No. 4,810,381 discloses a composite chromatographic article comprising a polytetrafluoroethylene (PTFE) fibril matrix and non-swellable sorptive particulate enmeshed therein. Other art disclosing polytetrafluoroethylene fibrillated matrix containing various particulate include U.S. Pat. Nos. 4,906,378, 4,871,671; 4,810,381; 4,565,663; 4,460,642; 4,373,519; 4,153,661; 3,407,249; and 3,407,096. Electrophoresis application is not taught or suggested in any of these references.

Processes for electrophoretic analyses are known. U.S. Pat. No. 4,006,069 discloses an electrophoresis process utilizing a supported analysis member comprising a porous polymeric flat plate and a polymeric gel enclosed in the open pores of the plate. Materials used include nonwoven fabrics. PTFE is not disclosed.

Japanese Patent No. 60-164,242 (English language abstract) discloses a process for a polyacrylamide gel film using a nonwoven polyester fabric. This process is also published in an article "Fabric Reinforced Polyacrylamide Gels for Electroblotting," in *Electrophoresis*, 6, 34-350, 1985.

Other patents of interest in electrophoretic applications include U.S. Pat. No. 3,922,432. This reference discloses a medium for a separation process prepared by bonding to the surface of a hydrated gel sheet a layer of discrete particles of a sorptive material. The particles themselves may be swellable so that they can become a continuous conductive medium for electrophoresis. U.S. Pat. No. 3,875,044 discloses a method of drying and adhering an electrophoresis gel to a polymer film backing and then precisely cutting sample wells into the gel. U.S. Pat. No. 4,657,656 discloses a method of increasing elasticity of polyacrylamide gels by adding a modifier such as glycerol to keep the gel elastic even when dry. U.S. Pat. No. 4,718,998 discloses a method of making a gel with an adhesive top and a thin polymer film overcoat useful for autoradiography. U.S. Pat. No. 4,722,777 discloses a method of making gels with improved adhesion to a polymer support backing using inorganic oxides in the adhesive.

SUMMARY OF THE INVENTION

Briefly, this invention provides a medium for electrophoresis comprising (a) a polytetrafluoroethylene (PTFE) fibril matrix, and (b) particulate, electrically mobile ions, and sufficient liquid in the interstitial spaces of said matrix to allow for ion transport, the ratio of said particulate to PTFE being in the range of 99:1 to 4:1 by weight, and said ions being present in said liquid in an amount to provide a solution of concentration in the range of 1 to 1000 millimolar.

Preferably, the medium is self supporting. Particulate can be swollen or non-swollen; preferably it is a swollen gel which together with the liquid and ions fills interstitial spaces in the PTFE matrix, so that gel material is enmeshed within the matrix. Preferably, gel material (particulate, liquid, and electrically mobile ions) comprises in the range of 90.000 to 99.999% by volume, more preferably 95.00 to 99.99, by volume of the electrophoresis medium.

In another aspect, this invention provides a method for electrophoretic analysis, the results of which can be used directly in blotting applications.

Media of the present invention have advantages compared to state-of-the-art materials. Fragile materials such as agarose and polyacrylamides can be incorporated into the fibrillated PTFE matrix to provide a dry precursor sheet that is stable in storage. When solvated, the media are dimensionally stable (i.e., has structural integrity) in the swollen or non-swollen state. The media are useful in both analytical and preparative (high loading capacity) modes of electrophoresis.

The background art has taught that fabric reinforced membranes are prepared from sols or monomer solutions which must then be polymerized. What the background art has not taught but what this invention teaches is that electrophoretic media, especially in the form of self supporting media, can be prepared from fibrillated PTFE, liquid, ions, and containing various particulate enmeshed therein. The media are useful in separation science. Preferred particulate are dry, prepolymerized and cross-linked materials. The result is that self supporting membranes for electrophoresis have structural integrity, can be uniformly fabricated to the size and shape desired (e.g., can be made flat, tapered, cylindrical, etc.) and for the kind of electrophoresis desired. Membranes of this invention allow electrophoresis media to be prepared in a shorter period of time compared to that of user prepared gels, and can be used with or without monomers that may be toxic (e.g., acrylamide is a neurotoxin).

Furthermore, because of the porosity of the present invention dry (not solvated) precursor sheet, the sheet can be easily and quickly solvated (generally involving hydration) and can be reverted to the dry state without loss of structural integrity. Moreover, particulates including swellable, insoluble, crosslinked materials such as cellulosics and cross-linked microporous dextrans, can be incorporated into PTFE fibril matrix by the technology of this invention, which is not possible by sol polymerization or by polymerization of soluble monomers after incorporation into a nonwoven material.

In summary, self supporting media of this invention are comprised of a fibrillated PTFE matrix with liquids, ions, and at least one of a variety of particulate enmeshed therein. The particulate is uniformly distributed throughout the medium. The media can be used directly for various forms of electrophoresis with demonstrated advantages over existing media such as:

dry precursor sheets and electrophoretic media have excellent structural stability;
they are easily handled, even when very thin or when a fragile particle is used in their preparation;
they are self supporting, have structural integrity, and do not require a polyester or other type of backing as a support;
dry precursor sheets can be stored in the dry state, can be quickly solvated and the resulting media are at least equivalent to conventional gels with respect to separations obtainable;
components separated by electrophoresis can be easily isolated and recovered, for example, by cutting and sectioning the composite medium or by electroblotting;
separation, isolation, concentration, and transfer of proteins or other components in a mixture can be effected in a single medium;
PTFE fibrils are inert, having a surface area of less than 1% of the surface area of the dry precursor sheet, and have minimal effect on the zeta potential (the potential across the diffuse layer of ions surrounding a charged surface) of the material (and resultant medium) to be used for electrophoresis;
media are ideally suited for electroblotting techniques known in the art. For preparative isoelectric focusing (IEF), the inventive precursor sheet can be solvated directly with an analyte solution of interest and thus avert transfer problems and dilutions;
media are inert to (that is, do not change their chemical state): analyte sorption and interactions, stains, dyes, detection methods, and electrical field.

In this application:
"particulate" means particle or particles;
"gel" means a disperse phase (i.e. particulate and ionic compound, but not PTFE) as a more or less rigid mass enclosing within it a liquid;
"PAGE" means polyacrylamide gel electrophoresis;
"IEF" means isoelectric focusing;
"dry precursor sheet" means a PTFE matrix having enmeshed therein particulate and optionally ionic compounds, also optionally including processing aids and excipients, in a dry state; the sheet has open spaces (voids) in the range of 30 to 70 volume percent;
"electrophoretic medium" means the dry precursor sheet with sufficient liquid (and ionic compound if not present in the precursor) to allow for ion transport; preferably the pores of the precursor are completely filled with liquid and particulate; more preferably at least 10 volume percent of the voids contain gel material;
"solvated" means a liquid that is in intimate contact with particulate, ions, and PTFE fibrils. It can swell particulate and fill remaining interstitial matrix spaces.
"electrically mobile ions" means ions, which when dissolved in a liquid, will migrate under the influence of an electric field;
"blotting" means the direct transfer of separated components from a separation medium to another medium (e.g., nitrocellulose); and
"electroblotting" means blotting wherein the driving force for transfer of separated components to a second medium is electrical potential.

BRIEF DESCRIPTION OF THE DRAWINGS

The Drawing is represented by FIGS. 1 and 2.

DETAILED DESCRIPTION OF PREFERRED EMBODIMENTS

Figure 1:
FIG. 1 is a scanning electron miorograph (SEM) of a commercially available polyacrylamide gel used in electrophoresis (enlarged 180×).

The ratio of particulate to PTFE in this invention media can be in the range of 99:1 to 4:1, preferably 49:1 to 4:1, and more preferably 48:1 to 9:1, by weight.

Particulate material (which can be one material or a combination of materials) useful in the present invention media is non-swellable or swellable in aqueous or organic liquid, and preferably is substantially insoluble in water or the electrophoretic liquid. Particulate can be charged or uncharged. Preferably, not more than 1.0 gram of particulate will dissolve in 100 g. of aqueous media (preferably distilled water) or organic liquid (preferably ethanol) into which particulate are mixed at 20° C. Particulate, which preferably are uncharged, and which can be swellable or non-swellable depending on the liquid, can be an organic compound such as acrylamide or a sugar, or an inorganic or organic salt, or a polymer such as hydrogels such as polyacrylamides and derivates thereof, polyvinylalcohols, polyacrylates, polymethacrylates, polyvinylpyrrolidone, styrenedivinylbenzene copolymer, agarose, agar, cellulosics such as end-capped cellulose and cellulose acetate, starch, dextrans, silica, polysaccharides, or particles coated with any of these materials. Preferred particulate are uncharged and are swellable and are capable of absorbing up to 2000 times their weight of liquid such as DMSO (dimethyl sulfoxide), and preferably water. More preferably, the particulate are gel-forming. Liquids in the media can swell the particulate and contribute to ion transport.

Particulates, which are commercially available, for example, from Sigma Chemical Co., St. Louis, Mo., Bio-Rad Laboratories, Richmond, Calif., Aldrich Chemical Co., Milwaukee, Wis., Pharmacia LKB Biotechnology, Inc., Piscataway, N.J., or Dupont de Nemours Chemical Corp., Wilmington, Del., may have a spherical shape, a regular shape or an irregular shape. Particulate which has been found useful in the invention has an apparent average size (diameter) within the range of 0.1 to about 600 micrometers, preferably in the range of 1 to 100 micrometers, more preferably 75 micrometers. It has been found advantageous in some instances to employ materials in two or more particle size ranges falling within the broad range. As an example, particles having an average size in the range of 0.1-30 micrometers having electrophoretic activity may be employed in combination with particles having an average size in the range 1 to 250 micrometers acting as a property modifier.

Some particle size reduction may take place during high shear mixing and calendering operations, depending upon the friability of particulate. Thus, while the particulate initially may be rather large, it may ultimately be reduced to a finer size in the final product.

Particulate useful in the present invention have sorptive capacity in the range of zero up to 2,000 times their weight, preferably in the range of greater than zero up to 500 times their weight. Hydrophilic particles which undergo dimensional changes due to swellability can be desirable when performing IEF.

In the dry state, particulate can be porous or non-porous.

As described in the method of U.S. Pat. No. 4,153,661, the active swellable or non-swellable particulate useful in the present invention can be pre-mixed with a property modifier which can function, for example, as processing aid or excipient. Representative non-swellable property modifiers (some of which may be soluble in water) can be calcium carbonate, ammonium carbonate, kaolin, polysaccharide, sugar, polyethylenes, polypropylenes, polymethacrylates, polyesters, polyamides (e.g. nylons), polyurethanes, polycarbonates, zeolites, cellulosics, silica, vermiculite, clay, ceramics, and chelating particles, and the like, and particles coated with such materials and combinations of these particulates. These property modifier materials can be present in an amount in the range of 0 to 28.99 parts per part of PTFE, preferably 0 to 9.00 parts per part of PTFE, provided that the swellable and/or non-swellable particles plus property modifiers (i.e. total particulate) do not exceed 99 parts particulate to 1 part PTFE. These ranges are desirable to achieve a preferred tensile strength of at least 1.0 kiloPascal (kPa) in the composite structure. Property modifiers can be active particulate depending on components in a medium.

Other non water-swellable property modifiers may be advantageously added to the mixture of the PTFE aqueous dispersion and the primary particulate material to provide further improvement in or modification of the composite media of the invention. For example, particulate modifiers can include electrophoretically inactive materials such as low surface area glass beads to act as property modifiers and processing aids. Coloring and/or fluorescent particulate can be added at low levels (up to 10 weight percent of particulate) to aid in visualizing separated sample components. In some cases, particulate which act as property modifiers are active in the electrophoretic process.

Liquids useful in providing the above-described aqueous-based liquids such as water, combinations of water and organic liquids such as water combined with alcohol (e.g., ethanol, methanol, glycerol, propylene glycol), acids such as trifluoroacetic acid, bases such amines, ampholytes such as Bio-Lyte TM (Bio-Rad), Pharmalyte TM (Pharmacia), Servalyte TM (Serva Chemical Co., Westbury, N.Y.), and dimethylsulfoxide. Nonaqueous based organic liquids useful in the present invention include nonpolar organic liquids such as toluene, and polar organic liquids such as acetonitrile, acetone, and alcohols of preferably 10 carbon atoms or less. Water is the preferred liquid.

Electrically mobile ionic compounds dissolved in the above-mentioned liquids for use in electrophoretic applications include bases such as amino acids, e.g., glycine, ammonium hydroxide, amines such as triethylamine; salts such as Tris-HCl (tris-hydroxymethylamino methane hydrochloride), aqueous and nonaqueous soluble borates (e.g., tetrafluoroborates), citrates, phosphates, and other buffers such as Good TM buffers (Sigma Chemical Company). Simple salts such sodium chloride, potassium chloride, alkali sulfates, carbonates, and nitrates, are also useful. Ionic compounds are present in the liquid so as to provide a solution having a concentration in the range of 1 millimolar to 1,000 millimolar, preferably 50 to 250 millimolar.

When the electrophoretically active particulate is hydrophobic, the preferred method of manufacture of the medium of the invention utilizes an emulsion of PTFE with a masking agent added to modify the hydrophobic particle surface/water interaction and allow rapid wetting of the surface of the hydrophobic particulate. Preferred masking agents are polar organic compounds such as alcohols, amines, acids, etc. with the preferred compounds being alcohols due to their efficacious removability as by solvent extraction or drying after formation of the dry precursor sheet.

Comparative FIG. 1 shows medium 10 having backing 12 and non-uniform polyacrylamide gel 14.

Figure 2:
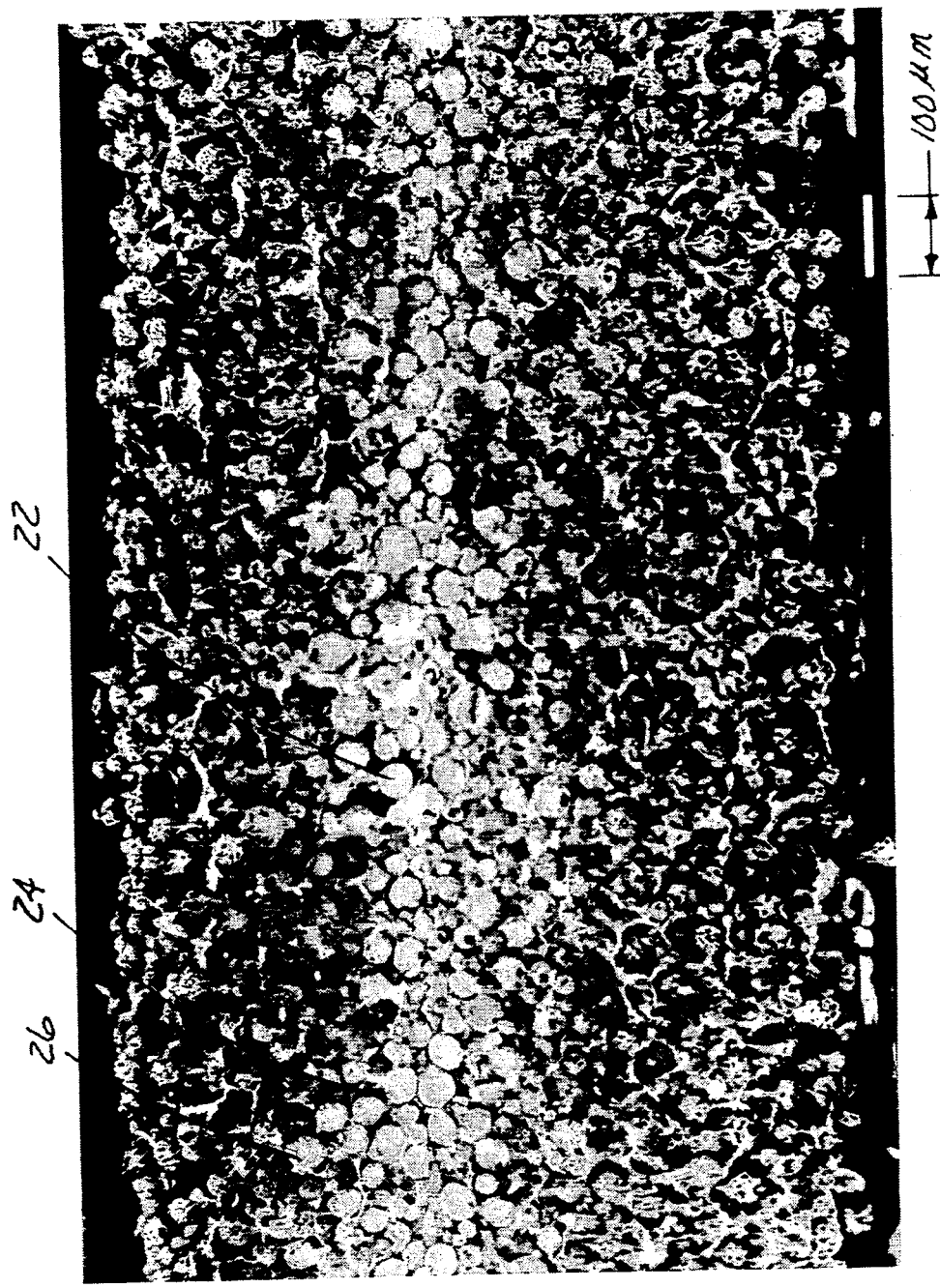
FIG. 2 is a scanning electron micrograph of a electrophoretic medium of the present invention comprising polytetrafluoroethylene fibril matrix with added particulate (polyacrylamide) and liquid enmeshed therein (invention) (enlarged 70×).

As can be seen in FIG. 2, medium 20 of the present invention is uniform and comprises PTFE matrix swollen particulate 22, and liquid containing ions in the interstitial spaces 24 of the matrix and in internal pores 26 of particulate (fibrils are too fine to be visible), particulate is uniformly distributed and enmeshed within the PTFE fibrils.

Specifically, the dry precursor sheet of the invention is prepared by dry blending the particulate or combination of particulates employed until a uniform dispersion is obtained and adding a volume of masking agent up to approximately one half the volume of the blended particulate. The aqueous PTFE dispersion, which may or may not contain additional masking agent, is then blended with the particulate/masking agent mixture to form a mass having a putty-like or dough-like consistency. Blending takes place along with sufficient lubricant water to meet but not exceed the sorptive capacity of the particles. Sorptive capacity of the solids of the mixture is noted to have been exceeded when small amounts of water can no longer be incorporated into the mass without separation. Care should be taken to ensure that the ratio of water to masking agent does not exceed 3:1. This condition should be maintained throughout the entire mixing operation. The putty-like mass is subjected to intensive mixing at a temperature maintained between about 20° C. and 100° C. for a time sufficient to cause initial fibrillation of the PTFE particles. Minimizing the mixing at the specified temperature is essential in obtaining electrophoretic transport properties. Mixing times will typically vary from 0.2 to 2 minutes to obtain the necessary initial fibrillation of the PTFE particles. Mixing causes partial fibrillation of a substantial portion of the PTFE particles.

Initial fibrillation will be noted to be at an optimum within 60 seconds after the point when all components have been fully incorporated together into a putty-like (dough like) consistency. Mixing beyond this point will produce a composite sheet of inferior electrophoretic properties.

Devices employed for obtaining the necessary intensive mixing are commercially available intensive mixing devices which are sometimes referred to as internal mixers, kneading mixers, double-blade batch mixers as well as intensive mixers and twin screw compounding mixers. The most popular mixer of this type is the sigma-blade or sigma-arm mixer. Some commercially available mixers of this type are those sold under the common designations Banbury mixer, Mogul mixer, C. W. Brabender Prep mixer and C. W. Brabender sigma blade mixer. Other suitable intensive mixing devices may also be used.

The putty-like mass is then transferred to a calendering device where the mass is calendered between rolls maintained at about 50° C. to about 100° C. to cause additional fibrillation and consolidation of the PTFE particles, while maintaining the liquid level of the mass at least at or near the absorptive capacity of the solids, until sufficient fibrillation occurs to produce the desired sheet material. Preferably the calendering rolls are made of a rigid material such as steel. A useful calendering device has a pair of rotatable opposed calendering rolls each of which may be heated and one of which may be adjusted toward the other to reduce the gap or nip between the two. Typically, the gap is adjusted to a setting of 10 millimeters for the initial processing of the mass and, as calendering operations progress, the gap is reduced until adequate consolidation of components occurs. At the end of the initial calendering operation, the sheet is folded and then rotated 90° to obtain biaxial fibrillation of the PTFE particles. Smaller rotational angles (e.g., 20 to less than 90°) may be preferred in some electrophoretic applications to reduce calendar biasing, i.e., unidirectional fibrillation and orientation. Excessive calendering in hydrophilic membranes (generally more than two times) in electrophoretic composites can increase hydrophobicity of the article surface, preventing hydration of enmeshed particles by aqueous liquids or buffers.

The calendered sheet is then dried under conditions which promote rapid liquid evaporation yet will not cause damage to the precursor sheet or any constituent therein. Preferably, drying is carried out at a temperature below 200° C. Preferred means of drying is by use of a forced air oven. The preferred drying temperature range is from 20° C. to about 70° C. The most convenient drying method involves exposing the composite sheet to air at room temperature for at least 24 hours. Drying time may vary depending upon the particular composition, some particulate materials having a tendency to retain liquid more than others. The resultant composite sheet has a tensile strength when measured by a suitable tensile testing device such as an Instron (Canton, Mass.) tensile testing device of at least 1.0 kPa and the sheet has a uniform porosity and a void volume of at least 30% of total volume.

A PTFE aqueous dispersion which can be employed in producing the PTFE composite medium of the invention is a milky-white aqueous suspension of minute PTFE particles. Typically, the PTFE aqueous dispersion will contain about 30% to about 70% by weight solids, the major portion of such solids being PTFE particles having a particle size in the range of about 0.05 to about 0.5 micrometers. Commercially available PTFE aqueous dispersion may contain other ingredients, for example, surfactant materials and stabilizers which promote continued suspension of the PTFE particles.

Such PTFE aqueous dispersions are presently commercially available from Dupont de Nemours Chemical Corp., Wilmington, Del., for example, under the trade names Teflon TM 30, Teflon TM 30B or Teflon TM 42 Teflon TM 30 and Teflon TM 30B contain about 59% to about 61% solids by weight which are for the most part 0.05 to 0.5 micrometer PTFE particles and from about 5.5% to about 6.5% by weight (based on weight of PTFE resin) of non-ionic wetting agent, typically octylphenol polyoxyethylene or nonylphenol polyoxyethylene. Teflon TM 42 contains about 32 to 35% by weight solids and no wetting agent but has a surface layer of organic liquid to prevent evaporation. It is generally desirable to remove, by organic liquid extraction, any residual surfactant or wetting agent after formation of the article.

To be useful as an electrophoretic medium, the dried precursor sheet is then saturated with a solution which provides the above-described medium which contains at least one electrically mobile ionic compound. The solution becomes an integral part of the resulting medium which when gelled generally has a consistency similar to that of raw beef liver or when non-gelled generally has a consistency similar to that of chamois cloth.

The present invention provides a novel electrophoretic medium and method therefor. In such a medium almost all of the particulate are separate one from another and each is isolated in a cage or cage-like structure that restrains the particulate on all sides by a fibrillated mesh of PTFE microfibers. The preferred dry precursor sheet of the invention has a thickness in the range of 125 to 10,0000 micrometers and has a tensile strength of at least 1.0 kPa and even as high as 13.6 mPa. The dry precursor sheet is substantially uniformly porous, making it suited for use, when solvated, as an electrophoretic medium which can be used as a single self-supporting medium or a combination of media to form a stack or as a composite having the medium adhered to a support such as glass, paper, metals, or polymers.

The media of the present invention can be a gelled electrophoretic medium or a non-gelled electrophoretic medium. Gelled media incorporate gel-forming particulate in fibrillated PTFE. Non-gelled media incorporate at least one of non-swellable and swellable particulate in fibrillated PTFE.

The self supporting structurally integrated composite electrophoretic medium comprises a polytetrafluoroethylene (PTFE) fibril matrix with at least one of swellable and non-swellable particulate enmeshed in the matrix and a process therefor. The self supporting composite medium retains the inherent separation characteristics of the added materials but affords several distinct advantages not foreseen or possible with conventional electrophoretic materials such as gel slabs.

A major advantage of the electrophoretic medium of this invention is the ability to incorporate non-rigid, non-self supporting materials such as agarose, sepharose, and polyacrylamides in a fibrillated PTFE matrix to provide a resultant self supporting electrophoretically useful medium which is superior to any related, existing membrane technology. Additional benefits of these media are:

1. The self supporting dry precursor sheet comprising fragile particulate (added material) entrapped in a fibrillated PTFE matrix has exceptional dimensional stability in both the dry and solvated form, compared to the particulate material itself.

2. Components of a mixture, separated by electrophoresis, can be readily recovered by cutting the separated component bands from the medium.

3. Separated components can be electrophoretically transferred (electroblotted) directly from the medium onto a suitable blotting membrane such as a piece of nitrocellulose paper or even another medium of this invention.

4. The medium has at least a factor of four higher loading capacity than that of conventional materials, making this technique very useful in the preparative mode.

5. The dry precursor sheet can be prepared and stored for extended periods of time without refrigeration and then can be rapidly activated (e.g., solvated by addition of liquid such as water, water containing buffers, organic liquids, and the like, as is known to those skilled in the art) prior to use. This represents substantial savings in terms of storage, transfer, shipping, time, and the like.

6. The precursor sheet when stored in a dried form, is not subject to microbial degradation.

7. The precursor sheet and medium are substantially more resistant to ripping or cracking during handling than is a conventional media.

Electrophoretic media of the present invention which are sheet-like articles having a thickness of 0.08 mm to 21 mm or thicker, preferably having a thickness in the range of 0.15 to 0.40 mm, can be used in any electrophoretic system using gel media, e.g. polyacrylamide gel electrophoresis (PAGE), native and sodium dodecyl sulfate (SDS) forms of PAGE, zone electrophoresis (using, for example agarose) immunological electrophoretic methods, granulated bed electrophoretic methods, and isoelectric focusing (IEF). As is known in the art, electrophoretic methods can be used to separate proteins, nucleic acids, DNA, dyes, polymers, or any other mixture of components that are separable based on at least one criterion of size, shape, or charge. Tensile strength of the media is at least 1 kPa.

In electrophoretic analysis, a sample comprising one or more components is applied to the solvated (preferably gel-like) medium of the present invention, and then an electric field is applied across the medium, the field being of sufficient strength and applied for a time sufficient to effect migration (preferably separation) of components.

Electrophoretically separated components can be further processed by means of blotting, including electroblotting. Further processing can also include probing the electroblotted species with antibodies (e.g. in the case of proteins, or other antigens), hybridization with radioactive or colored probes (e.g. for DNA), and the like.

Blotting is a technique for the transfer of electrophoretically separated species from a separation medium to a blotting membrane (e.g., nitrocellulose). Materials which are commonly blotted include proteins, carbohydrates, lipids, DNA, RNA, and dyes. Blotting transfers species from the surface and internal regions of a separation medium to the surface of a blotting membrane, where the species bind tightly. This surface binding facilitates detection of bound species. Detection is accomplished with probes which are specific for the bound species. Probes are labeled for easy visualization. Probes can be radioactive, colored, fluorescent, or enzymatically active. There are two main forms of blotting: capillary and electroblotting. In capillary blotting, mass flow of liquid through the separation medium carries the separated species to the blotting membrane where they bind tightly to the surface of the membrane. In electroblotting, an electrical field drives the separated species from the separation medium to the blotting membrane where they again bind tightly to the surface.

Electrophoretic media of the present invention are self supporting, and remain tough and flexible in the solvated or dry precursor state. They can be easily handled even when very thin or when a low particulate content is used requiring no polyester or other type of backing. Fibrillated PTFE-containing media are also ideally suited for electroblotting the electrophoretically separated species. Dry precursor sheets can be stored in the dry state and can be quickly solvated before use, thus saving a substantial amount of time normally required to prepare and polymerize a conventional gel.

In preparative isoelectric focusing (IEF), dry precursor sheets of this invention can be solvated directly with the analyte solution of interest which averts transfer problems and dilutions. After electrophoretic separation of the sample into its component parts is accomplished, components can be easily isolated by cutting the solvated sheet with a razor blade or scissors and recovering the analytes as is known to those skilled in the art. Separation, isolation, and concentration of proteins or other components in a mixture can be effected in a single, rather than multiple steps.

Dry precursor sheets are inert to chemical and sorptive interaction, and PTFE fibrils therein have a surface area of less than 1%, and have minimal effect on the zeta potential of the electrophoretic medium.

The medium can be used alone or in combination with another medium to form a discontinuous electrophoretic medium which comprises a stacking gel and a separating gel in physical contact with each other.

Objects and advantages of this invention are further illustrated by the following examples, but the particular materials and amounts thereof recited. In these examples, as well as other conditions and details, should not be construed to unduly limit this invention.

EXAMPLES

The following examples show that media of this invention can be used as self supporting media for various forms of electrophoresis. A fibrillated PTFE matrix serves as a binder to which a variety of particulates can be added directly or with further modification. Use of PTFE-containing membranes as media for electrophoresis demonstrated clear advantages over conventional gel media.

Methods and materials (general)

In these examples, 5 cm square media were used in a Pharmacia automated electrophoresis PhastSystem TM (Pharmacia LKB Biotechnology, Inc., Piscataway, N.J.); however, virtually any size or shape (including tube gels) can be prepared using PTFE-containing media technology so that any commercial or customized electrophoresis unit could be used.

Electrophoresis experiments were performed in a PhastSystem using conditions listed below. Instrument temperature was maintained at 0° to 15° C. Ampholytes for isoelectric focusing were Bio-lyte 3/10 (Bio-Rad Laboratories, Richmond, Calif.). Media were prepared using agarose and cross-linked polyacrylamide beads (75 micrometer average diameter) from Bio-Rad Laboratories. Standard mixtures of proteins were from Bio-Rad (IEF Standards pH 4.6–9.6 or prepared from individual proteins from Sigma Chemical Company, St. Louis, Mo.). All other chemicals were electrophoresis grade. All of the media of this invention were prepared as detailed in the appropriate examples below. Trials where further modifications of the media were made are noted appropriately.

All amounts are by weight unless otherwise indicated. All media had tensile strength of at least 1.0 kPa in the solvated and dry state.

ELECTROPHORESIS SEPARATION EXAMPLES

Example 1

Isoelectric Focusing in Agarose-PTFE-containing Media

A dry precursor sheet containing 10% PTFE, 88.2% sucrose, and 1.8% agarose was prepared as follows: Dry sucrose and agarose (Bio Rad, Richmond, Va.) particulate were blended together in a beaker. 5 grams of ethanol were then added to the mixture and distributed uniformly. 3.7 grams of PTFE emulsion (Teflon 30B) were added slowly while the mixture was being stirred. When all the PTFE was added, the resulting putty-like mass was vigorously stirred by hand for 60 seconds. The mass was then transferred to a two-roll mill for further processing. After a series of biaxial calendering steps, the distance between rolls was reduced in a programmed sequence until a sheet with a thickness of 0.5 mm (21 mils) was produced.

The sheet was boiled for 15 minutes in water to dissolve the sucrose and to hydrate the agarose. The medium was then washed with cool water for 15 minutes and placed in a solution containing 2.4% v/v ampholyte solution (water) (Bio-Lyte TM 3/10, Bio Rad, Richmond, Calif.) and 5% v/v glycerol. Isoelectric focusing was then performed. A pH gradient was first generated using a 200 volt field (3.5 watt max.) for 25 volt hours. A sample of standard protein mixture (Bio-Rad IEF Standards) containing about 10 micrograms of each of 8 different proteins was spotted onto the media and a 200 volt field was applied for 80 volt hours. The separated proteins were then visualized using Crocein Scarlet stain (Aldrich Chemical Co., Milwaukee, Wis.). The eight proteins in the mixture were clearly separated. The medium remained tough and flexible both when wet and after drying.

Example 2

Isoelectric Focusing in Polyacrylamide-PTFE-containing Medium

A precursor sheet containing 90% cross-llinked polyacrylamide and 10% PTFE was prepared as follows: Dry polyacrylamide particulate (75 micrometer average diameter) (Bio Rad, Richmond, Va.) was placed in a beaker. 20 grams of ethanol were added to 3.7 grams of PTFE emulsion (Teflon 30B) and slowly stirred until the PTFE emulsion began to agglommerate. While the mixture was being continuously stirred, the ethanol/PTFE solution was added rapidly to the polyacrylamide particulate. When all the PTFE was added, the resulting putty-like mass was vigorously stirred by hand for 60 seconds. The mass was then transferred to a two-roll mill for further processing. After a series of biaxial calendering steps, the distance between rolls was reduced in a programmed sequence until a sheet with a thickness of 0.15 mm (7 mils) was produced. The dry precursor sheet (75 micrometer average diameter) was placed in a solution containing 4% v/v ampholytes in water and 25% v/v glycerol for 15 minutes. Excess liquid was removed from the medium with tissue paper, and the medium was placed into the PhastSystem. A pH gradient was formed in the medium using a 400 volt gradient for 10 volt hours after which 50 and 100 microliter aliquots of the standard protein (Bio-Rad IEF standard mixture) mixture were applied and focused first at 40 volts for 1 volt hour followed by 1000 volts for 400 volt hours. An excellent separation of the proteins in the mixture was achieved. Even minor components of the hemoglobin band in the Bio-Rad IEF standard mixture were resolved. The medium remained tough and flexible both when wet and after drying.

Example 3

Preparative Isoelectric Focusing

A 0.2 cm thick dry precursor sheet was prepared from the 10% PTFE and 90% polyacrylamide composition as described above. A 4.56 cm square piece of the sheet was solvated with a solution of 25% v/v glycerol and 4% v/v ampholyte solution (Bio-Lyte 3/10) in water for one hour. Thickness of the medium at this point had increased to about one cm thick. Its length and width, however, had only increased from about 4.5 to 5.5 cm. Excess liquid was then pressed out of the medium by gently pressing it between sheets of paper towels. A sample containing 250 mg each of equine cytochrome C, equine myoglobin, and bacterial glucose oxidase in 6 ml of a 25% glycerol, 4% ampholyte solution was then pipetted onto the medium, which was then placed in the automated electrophoresis PhastSystem and isoelectric focusing performed at 200 volts for three hours. About halfway through the process, the gel was flipped over to increase resolution. The medium was then removed and examined.

Electrophoresis separated the three proteins as three separate, sharp bands across the medium. After cutting these separated bands out of the medium with a razor blade, the respective proteins were recovered by homogenizing the protein band in a test tube with a stirring rod and then suction filtering the pulp to remove the protein which was subsequently shown by conventional isoelectric focusing to be pure. When dried, the medium remained tough and flexible. In a similar experiment, the dry precursor sheet was solvated in a protein mixture solution to which ampholytes had been added. IEF was then performed directly on this medium and the proteins were separated in a similar fashion as above.

Example 4

SDS Discontinuous Gel Electrophoresis

Example 4 teaches the separation of proteins utilizing a medium prepared from two separate dry precursor sheets, each containing a different amount of acrylamide monomer and each at a different pH. In one operation the two are joined by polymerizing at one common side. One serves as the stacking gel and one as the separating gel, as is known to those skilled in the art. Heretofor, this operation required two steps: polymerizing the separating gel and then layering over it a stacking solution which, in turn, was polymerized to provide the stacking gel.

Two dry precursor sheets, 0.19 mm (7 mil) thick and containing 10% PTFE and 90% polyacrylamide beads (Bio Rad, Richmond, Calif.) were solvated in 12% and 4% acrylamide solutions, respectively. These solutions contained the following:
12% Solution
   10.0 mL 1.5 M Tris-HCl buffer at pH 8.8
   0.4 mL 10% sodium dodecylsulfate (SDS)
1 16.0 mL stock acrylamide solution*
   0.2 mL 10% ammonium persulfate solution
   0.02 mL tetramethylenediamine (TEMED)
   13.4 mL water
4% Solution
   5.0 mL 0.5 M Tris-HCl at pH 6.8
   0.2 mL 10% SDS
   2.6 mL stock acrylamide solution*
   0.1 mL 10% ammonium persulfate solution
   0.02 mL TEMED
   12.2 mL water
*Acrylamide stock solution in both formulations contained 29.2% acrylamide monomer and 0.8% N,N′-methylene-bisacrylamide in water.

The straight edges of the two media were placed in contact with each other and polymerization allowed to proceed. After polymerization (initiated by the ammonium persulfate), the media were found to be securely bonded to each other. A standard 5 cm square medium was then cut from this joined medium such that the upper quarter was from the 4% (low pH) medium. This portion served as the stacking gel. A sample of a mixture of bovine serum albumin, bacterial glucose oxidase, and equine myoglobin (100 micrograms each) in SDS was applied to the stacking buffer and electrophoresis was carried out at 300 volts for 100 volt hours. The medium was then treated with a Coomassie blue stain (Aldrich Chemical Co., Milwaukee, Wis.) and examined. The three proteins were clearly separated according to molecular weights.

The same experiment was repeated but the acrylamide solution, TEMED, and ammonium persulfate were not used. The low pH medium was again used as the stacking gel, only this time it was merely pressed up against the separating gel. Again, the proteins clearly separated according to their molecular weights. These data show that merely physically contacting the stacking gel to the separating gel was sufficient to achieve electrophoretic separation of the mixture into its components.

Example 5

Electroblotting of Colored Proteins from IEF Polyacrylamide PTFE Medium onto a Nitrocellulose Membrane.

A dry precursor sheet composed of 10% PTFE and 90% crosslinked polyacrylamide beads (75 micrometer average diameter) was solvated in a solution containing 4% ampholytes and 25% glycerol for 10 minutes. Excess liquid was removed from the medium with tissue paper and the medium was placed into the Phast System ™. A pH gradient was generated in the medium using a 400 volt electrical gradient for 10 volt hours. Ten microliters of Bio-Rad IEF standard protein mixture was then placed onto the medium, and the proteins were separated using a 1000 volt gradient for 400 volt hours. The IEF medium was then placed on a nitrocellulose blotting membrane pre-wetted with transfer buffer (9.08 gram Tris, 43.23 gram glycine, 750 ml methanol and 3 liters of water pH 8.3). Several layers of filter paper soaked in transfer buffer were placed on either side to sandwich the IEF medium and nitrocellulose membrane and the sandwich was placed in a blotting tank. The IEF gel was blotted 12 hours at 50 volts. After the nitrocellulose membrane was removed from the sandwich, the blotted proteins (colored) were visible on the surface of the nitrocellulose membrane.

Example 6

Electroblotting of Human Anti-Thrombin 3 Protein from a Polyacrylamide PTFE Medium to a Nitrocellulose Membrane with Immune Detection.

A polyacrylamide PTFE dry precursor was prepared and processed as in Example 5 with the exception that the protein used was human anti-thrombin 3 protein (AT3, Sigma Chemical Co., St. Louis, Mo.) rather than the IEF standard proteins. Blotting to nitrocellulose was performed as in Example 5. Detection of the blotted AT3* was accomplished by double immunological probes. The nitrocellulose membrane (after blotting) was placed in phosphate buffered saline with Tween ™, available from Bio Rad, Richmond, Calif., nonionic surfactant (PBS-T) for 1 hour. The membrane was then placed in a 1 to 50 dilution in PBS-T of goat anti-human AT3 for 1 hour. This antibody (IgG)* specifically reacts with (binds to) human AT3. The membrane was then washed in buffer A (50 mM Tris, 1 mM MgCl₂ pH 9.3) for 1 hour. The membrane was then placed in a 1 to 500 dilution in buffer A of rabbit anti-goat IgG* conjugated to alkaline phosphatase for 1 hour. (This antibody specifically reacts with goat IgG and has alkaline phosphatase activity.) The membrane was then washed in buffer A for 1 hour. The bound human AT3 was visualized by incubating the nitrocellulose membrane in buffer A containing 5-bromo-3-chloroindolyl phosphate (BCIP)* and nitro blue tetrazolium (NBT)*. These two compounds reacted at alkaline pH in the presence of phosphatase enzyme to produce a purple color at the site on the nitrocellulose where the phosphatase was bound. The phosphatase was covalently bound to the rabbit anti-goat IgG protein, which in turn was bound to the goat anti-human AT3, which in turn was bound to the AT3 on the nitrocellulose surface. This cascade of binding ensured that only AT3 was detected as a purple band on the nitrocellulose.

*Goat anti-human AT3, rabbit anti-goat IgG conjugate with alkaline phosphatase, BCIP, and NBT, all purchased from Sigma Chemical Co., St. Louis, Mo.

Various modifications and alterations of this invention will become apparent to those skilled in the art without departing from the scope and spirit of this invention, and it should be understood that this invention is not to be unduly limited to the following illustrative embodiments set forth herein.

We claim:

1. A medium for electrophoresis comprising
   (a) a polytetrafluoroethylene (PTFE) fibril matrix, and
   (b) particulate having an average size in the range of 1 to 600 micrometers electrically mobile ions, and sufficient liquid in the interstitial spaces of said matrix to allow for ion transport,
   the ratio of said particulate to PTFE being in the range of 99:1 to 4:1 by weight, and said ions being present in said liquid in an amount to provide a solution of concentration in the range of 1 to 1000 millimolar, and wherein almost all of said particulate are separate one from another and are isolated in cages or cage-like structures of PTFE microfibers.

2. The medium according to claim 1 wherein said particulate is polymeric.

3. The medium according to claim 2 wherein said particulate is polyacrylamide.

4. The medium according to claim 1 wherein said particulate is organic.

5. The medium according to claim 1 wherein said particulate is inorganic.

6. The medium according to claim 1 wherein said particulate is uncharged.

7. The medium according to claim 1 wherein said particulate is charged.

8. The medium according to claim 1 wherein said particulate is at least one of polyacrylamide, agarose, agar, end-capped cellulose, cellulose acetate, starch, polysaccharide, and sugar.

9. The medium according to claim 1 wherein said particulate is selected from the group consisting of agarose, agar, polyacrylates, polymethacrylates, styrene-divylbenzene copolymers, polyacrylamides, polyvinylacohol, polyvinylpyrrolidone, and particles coated with these materials.

10. The medium according to claim 1 further comprising at least one property modifier.

11. The medium according to claim 10 wherein said property modifier is present in the range of greater than 0 and up to 28.99 parts per part PTFE, provided that the total particulate does not exceed 99 parts particulate to 1 part PTFE.

12. The medium according to claim 10 wherein said modifier particles are selected from the group consisting of calcium carbonate, ammonium carbonate, kaolin, sugar, polyethylenes, polypropylenes, polymethacrylates, polyesters, polyamides, polyurethanes, polycarbonates, zeolites, cellulosics, silica, polysaccharide, vermiculite, clay, ceramics, chelating particles, and particles coated with these materials.

13. The medium according to claim 1 wherein said liquid is aqueous-based.

14. The medium according to claim 1 wherein said liquid is organic.

15. The medium according to claim 13 wherein said aqueous-based liquid comprises at least one of an alcohol, an acid, a base, or a combination of water and organic liquid.

16. The medium according to claim 13 wherein said liquid is water.

17. The medium according to claim 1 wherein said electrically mobile ionic compound is selected from the group consisting of acids, bases, and salts.

18. The medium according to claim 1 wherein said solution has a mobile ionic concentration in the range of 50 to 250 millimolar.

19. The medium according to claim 1 which is a separating gel.

20. The medium according to claim 1 which is a stacking gel.

21. The medium according to claim 10 which is a combination of stacking gel and a separating gel to provide a discontinuous electrophoretic medium.

22. The medium according to claim 1 which is a gel electrophoretic medium.

23. The medium according to claim 1 which is self-supporting.

24. A medium for electrophoresis comprising
   (a) a polytetrafluoroethylene fibril matrix, and
   (b) polyacrylamide particulate having an average size in the range of 1 to 100 micrometers, electrically mobile ions, and sufficient water in the interstitial spaces of said matrix to allow for ion transport,
   the ratio of particulate to polytetrafluoroethylene being in the range of 99:1 to 4:1, and said ions being present in said liquid in an amount to provide a solution of 1 to 1000 millimolar, and wherein almost all of said particulate are separate one from another and are isolated in cages or cage-like structures of PTFE microfibers.

25. A method for electrophoresis comprising the steps:
   (a) applying a sample comprising one or more components onto a medium comprising a polytetrafluoroethylene fibril matrix and at least one of non-swellable and swellable particulate having an average size in the range of 1 to 600 micrometers, electrically mobile ions, and sufficient liquid in the interstitial spaces of said matrix to allow for ion transport, the ratio of particulate to polytetrafluoroethylene being in the range of 99:1 to 4:1 by weight, said ions being present in said liquid in an amount to provide a solution of concentration in the range of 1 to 1000 millimolar, and wherein almost all of said particulate are separate one from another and are isolated in cages or cage-like structures of PTFE microfibers, (b) applying an electric current to said medium of sufficient strength and for a time sufficient to effect separation of the components of said sample.

26. The method according to claim 25 wherein said medium comprises particulate which is at least one of acrylamide, polyacrylamide, agarose, agar, end-capped cellulose, cellulose acetate, starch, and sugar.

27. The method according to claim 25 further comprising the step of subjecting said separated components to electroblotting.

28. The method according to claim 25 further comprising the step of individually cutting each separated component from said medium.

29. The method according to claim 27 further comprising the step of individually cutting each separated component from said medium.

30. The method according to claim 25 wherein said liquid is aqueous-based.

31. The method according to claim 25 wherein said liquid is organic.

32. The medium according to claim 1 wherein said particulate has an average size in the range of 1 to 100 micrometers.

33. The method according to claim 25 wherein said particulate has an average size in the range of 1 to 100 micrometers.

34. The medium according to claim 1 which has been dried to provide a medium for electrophoresis which is uniformly porous.

* * * * *

UNITED STATES PATENT AND TRADEMARK OFFICE
CERTIFICATE OF CORRECTION

PATENT NO. : 5,019,232
DATED : May 28, 1991
INVENTOR(S) : Theresa J. Wilson et al.

It is certified that error appears in the above-identified patent and that said Letters Patent is hereby corrected as shown below:

Col. 6, line 54, after "such" kindly insert -- as --.

Col. 11, line 18, "recited. In" should read -- recited in --.

Col. 13, line 54, "1 16.0" should read -- 16.0 --.

Col. 15: Claim 1, line 5 of the claim, add a comma after "600 micrometers".

Col. 15: Claim 9, line 4, "styrene-divylbenzene" should read -- styrene-divinylbenzene --.

Signed and Sealed this

Seventeenth Day of August, 1993

Attest:

BRUCE LEHMAN

Attesting Officer          Commissioner of Patents and Trademarks